United States Patent [19]

Hayes

[11] Patent Number: 5,470,758
[45] Date of Patent: Nov. 28, 1995

[54] LARGE CYTOLOGY SAMPLE CHAMBER FOR DISTRIBUTING MATERIAL ONTO A MICROSCOPE SLIDE

[75] Inventor: William J. Hayes, Edgeworth, Pa.

[73] Assignee: Shandon, Inc., Pittsburgh, Pa.

[21] Appl. No.: 355,630

[22] Filed: Dec. 14, 1994

[51] Int. Cl.[6] .................................................. G01N 9/30
[52] U.S. Cl. ........................... 436/177; 422/72; 422/102; 422/104; 436/45; 436/99; 210/787; 210/788; 210/789; 210/512.1; 220/501; 220/563; 494/16; 494/20
[58] Field of Search ........................... 422/72, 102, 104; 436/45, 99, 177; 210/787, 788, 789, 512.1; 220/501, 563; 494/16, 20; 366/337, 340

[56] References Cited

U.S. PATENT DOCUMENTS

| D. 292,433 | 10/1987 | Griffin | D24/22 |
|---|---|---|---|
| D. 306,480 | 3/1990 | Gordon et al. | D24/22 |
| 1,491,049 | 4/1924 | Lichtenthaeler | 366/340 |
| 2,704,206 | 3/1955 | Crook | 366/340 |
| 3,045,984 | 7/1962 | Cochran | 366/340 |
| 3,620,506 | 11/1971 | So | 366/337 |
| 4,197,329 | 4/1980 | Holyroyd et al. | 427/2 |
| 4,207,009 | 6/1980 | Glocker | 366/340 |
| 4,344,562 | 8/1982 | Ricci | 233/26 |
| 4,391,710 | 7/1983 | Gordon | 210/361 |
| 4,414,197 | 11/1983 | Dussault | 424/3 |
| 4,498,410 | 8/1984 | Zeya | 427/2 |
| 4,591,486 | 5/1986 | Eberle | 422/72 |
| 4,678,579 | 7/1987 | Griffin | 210/477 |
| 4,696,743 | 9/1987 | Gordon et al. | 210/361 |
| 4,705,630 | 11/1987 | Gordon et al. | 210/361 |
| 4,729,778 | 3/1988 | Griffin | 65/36 |
| 4,783,319 | 11/1988 | Hobrich et al. | 360/340 |
| 4,788,154 | 11/1988 | Guigan | 436/180 |
| 4,812,294 | 3/1989 | Combs | 422/72 |
| 4,814,282 | 3/1989 | Holen et al. | 436/165 |
| 4,853,188 | 8/1989 | Toya | 210/512.1 |
| 5,143,627 | 9/1992 | Lapidus et al. | 210/767 |
| 5,252,228 | 10/1993 | Stokes | 210/781 |
| 5,256,376 | 10/1993 | Callan et al. | 422/104 |
| 5,380,435 | 1/1995 | Stokes et al. | 210/361 |

Primary Examiner—James C. Housel
Assistant Examiner—Sharidan Carrillo
Attorney, Agent, or Firm—John E. Reilly

[57] ABSTRACT

A cytology chamber comprises a sample holding portion, a funnel through which the fluid sample is directed into the holding portion of the chamber, a generally flat, solid flange member defining an upright support surface and having an opening through the flange member in communication with the holding portion, and baffle plates in the holding portion define a tortuous path of flow for collecting at least some of the sediment in the fluid prior to reaching the bottom of the holding portion.

16 Claims, 2 Drawing Sheets

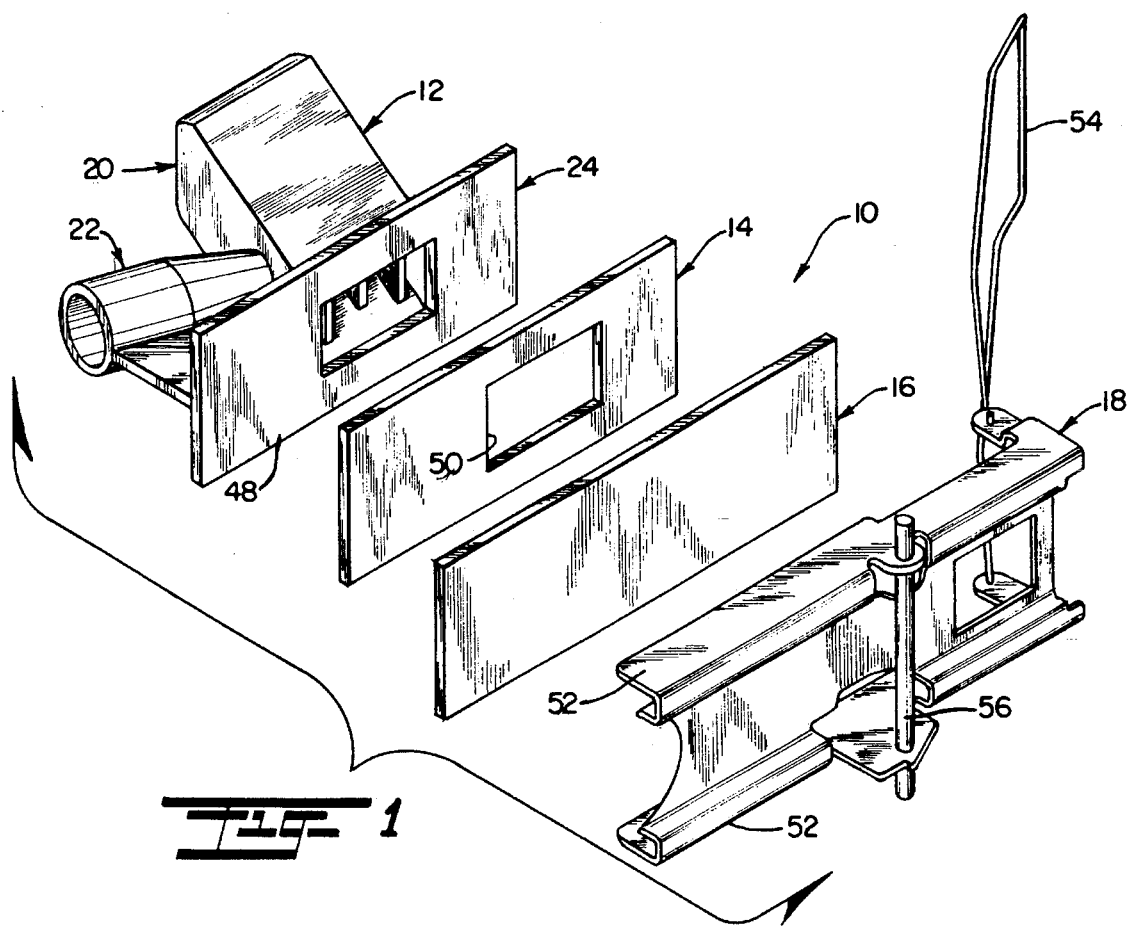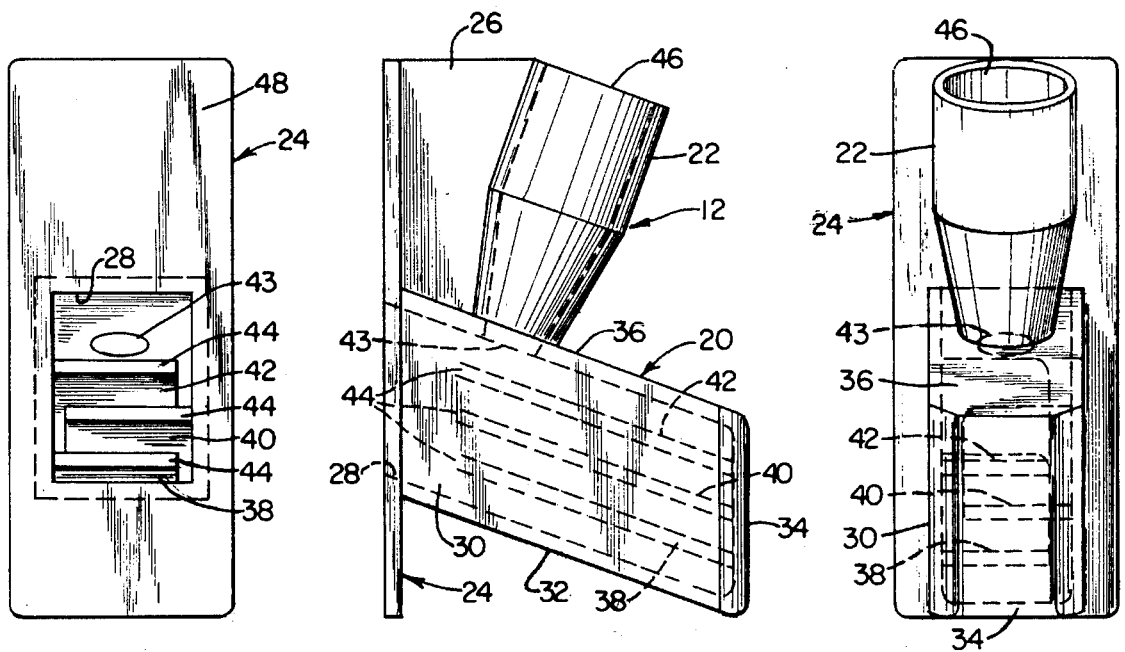

LARGE CYTOLOGY SAMPLE CHAMBER FOR DISTRIBUTING MATERIAL ONTO A MICROSCOPE SLIDE

BACKGROUND AND FIELD OF INVENTION

This invention generally relates to cytocentrifuge sample chambers and more particularly to a novel and improved cytology chamber and method for distributing biological material on a microscope slide during the centrifugation of body fluid samples.

Cytocentrifuges are small, precision centrifuges which are particularly designed for centrifuging blood and other body fluid samples in order to separate these fluids into various components. These machines are typically used to deposit sediment materials such as cellular structures onto the surface of a microscope slide for further detailed microscopic study.

A cytocentrifuge has a removable head typically containing an even number of sample chamber assemblies in a carrier and spaced symmetrically about the centrifuge axis. The head has a removable top and an annular bowl shaped bottom. The bottom of the head supports the carrier which positions the chamber assemblies symmetrically around the inside of the annular bowl. When the top is installed on the bottom, all of the sample chamber assemblies are completely sealed inside. The assembled head is then installed in the cytocentrifuge for the centrifugal operation.

Typical cytocentrifuge or cytology chambers for centrifugation of biological fluid samples are disclosed in U.S. Pat. Nos. 4,788,154; 4,814,282; 4,391,710; 4,678,579 and 4,729,778. Each of the chambers in the latter two of these patents is actually an assembly of the chamber, a microscope slide, and a holder which includes a retaining spring bracket removably fastening the slide to the chamber and a pivot means for rotatably mounting the assembly in the carrier in the cytocentrifuge head.

A filter card may be placed between the chamber and the microscope slide for such purposes as to absorb the suspending fluid during centrifugation. Each chamber includes a funnel portion through which a fluid sample may be introduced via pipette, a sample holding portion for receiving at least a portion of the sample passing through the funnel, and a flat flange portion having a discharge opening in communication with the holding portion. The flat flange portion is designed to mate against one surface of the microscope slide. The holder is basically a channel shaped sheet metal member which receives the slide, the filter card and the flange portion of the chamber therein and has a wire spring clip which releasably holds them together in the channel. The holder also includes a bar mounted across the channel member that fits horizontally into corresponding recesses in the carrier in the bottom portion of the cytocentrifuge head so that the assembly is free to partially rotate about the horizontal axis of the bar.

The assemblies are balanced, at rest, in the centrifuge head in a tilted position such that the funnel and holding portions containing the fluid sample are inclined away from the microscope slide to keep the sample from the filter and/or microscope slide. Only during operation of the cytocentrifuge does the assembly pivot to an upright, vertical position, allowing the fluid to be centrifugally forced outward, through the discharge opening and against the filter material and/or the slide surface.

The loading of a cytocentrifuge is performed in the following manner: First, empty cytology sample chambers are assembled to a microscope slide each with a filter card between the flange member and the microscope slide and clamped together in the channel shaped chamber holder. The empty chamber assemblies are then placed into the carrier in the bottom of the head. Finally, the samples are sequentially introduced into the chambers. Since the chamber holders tilt the chambers as above described, the samples in each chamber remain spaced from their respective slide surfaces.

The operation of loading the samples into the chambers takes a finite period of time. During this time period, the heavier cellular material suspended in each of the previously loaded fluid samples tend to sediment to the bottom of the holding portion of the sample chamber. When the samples are then centrifuged, even if the samples loaded were identical, there may be differing amounts of cellular material deposited onto the slides, depending on the amount of prior sedimentation that has taken place in each chamber. In addition there may be a nonuniform distribution of cellular material on each slide with a higher concentration toward the slide surface region adjacent the bottom of the holding portion of the chamber. These disparities and discrepancies between slides prepared from otherwise identical samples are undesirable. They are minimized by keeping the sample volumes extremely small, on the order of one millimeter or less, and minimizing the surface area of the slide which is covered by the discharge opening. In addition, care is taken to minimize the time taken to load the centrifuge sample chambers with samples prior to centrifuging. These sample size limitations can limit the cellular concentration levels which may be detected and therefore the accuracy of and time and labor required for some analyses. In addition, it would be more efficient to centrifuge a larger sample volume if it weren't for the effects of prior sedimentation during sample loading. Thus there is a need for being able to centrifuge larger sample volumes, for example, in order to detect smaller concentrations of specific biological materials. There is also a need for a method to reduce the effects of sedimentation during chamber loading and for providing a more uniform distribution of cellular material onto a microscope slide during centrifugation.

The novel method and improved large volume cytology (or cytocentrifuge) chamber in accordance with the present invention meets these needs by ensuring a more even distribution of biological material on the surface of a microscope slide during centrifugation.

SUMMARY OF THE INVENTION

The method in accordance with the present invention to reduce the effects of sedimentation during chamber loading basically comprises the steps of directing the liquid sample into a cytology sample chamber fastened to a microscope slide along a tortuous path of spaced surfaces in the chamber to reach the bottom of the chamber, each of the surfaces being in communication with a common discharge opening from the chamber to one surface of the microscope slide; permitting some of said biological material to settle as sediment on these path surfaces; and centrifuging the sample chamber. The sedimented biological material on each of the path surfaces is simply passed, via centrifugal force, directly through the immediately adjacent portion of the discharge opening onto the surface of the slide. In this way, a distributed deposition of biological material is achieved.

A preferred embodiment of the cytology chamber in accordance with a first aspect of the present invention is a unitary disposable sample chamber for receiving a sample of biological material in a liquid suspension. The chamber comprises a sample holding portion, a liquid suspension-receiving funnel through which the sample is directed into the holding portion of the chamber, and a generally flat, solid flange member defining an upright support surface from which the holding portion and funnel are supported and having an opening in the flange member in communication with the holding portion.

The holding portion has a pair of spaced vertical sidewalls, a bottom wall cantilevered and downwardly sloping from the upright flange at an acute angle, a top wall merging with the funnel and a back wall spaced from the opening through the flange. The holding portion also has staggered baffle means therein for directing the sample from the funnel along a tortuous path of surfaces to the bottom of the holding portion. This provides the spaced surfaces upon which the biological material may settle.

The baffle means preferably comprises a plurality of elongated plates spaced from each other above the bottom wall, each having one end supported from the back wall of the holding portion. Each of the plates is also supported from one or the other of the sidewalls in an alternating fashion. The other, upper end of each of these plates is free, facing toward the opening between the holding portion and the flange portion, permitting free fluid passage thereover. The baffle plates are preferably oriented parallel to the bottom wall of the holding portion which is cantilever supported at an acute angle from the flange member. When the chamber is oriented with the flange member generally upright, the holding portion slants downward at an acute angle away from the flange member. Thus any liquid sample entering the holding portion through the funnel, which passes through the top wall of the holding portion, is directed via gravity away from the flange portion. The liquid sample must pass back and forth over the surfaces of each of the internal baffle plates in order to reach the bottom wall where the sample volume accumulates.

This construction of the holding portion thus provides a large surface area over which sedimentation can occur. During centrifugation, the sedimented material slides along the plate surfaces and off the free ends, then directly through the discharge opening to the slide surface. Since the free ends of the plates are spaced apart, generally spanning the discharge opening, material passing over the ends and through the discharge opening will be distributed to the directly adjacent surface portion of the slide against the discharge opening.

In accordance with a second aspect of the present invention, a seal is provided around the discharge opening through the flange member to prevent leakage of the sample suspension medium from the assembly. In contrast, in conventional cytocentrifuge chambers no seal is provided nor is one necessary since the sample volume is very small and the suspension medium is totally absorbed by the filter card. However, in the present invention, a significantly larger sample volume is used, on the order of up to 6 milliliters. Accordingly, a seal must be provided to prevent leakage and spillage of the fluid during centrifugation. This seal is preferably a sheet of closed cell foam sandwiched between the microscope slide and the flange member portion of the chamber. The seal has an aperture therethrough in registry with and preferably corresponds in shape and size to the discharge opening.

The microscope slides utilized in the present invention are preferably coated with a material, such as, albumin or is electrically charged so that cellular material that reaches the surface will be retained thereon. When the cytocentrifuge is turned on, the sample volume is directed against the microscope slide by centrifugal force. The sedimented cells are oppositely charged to that of the slide surface. Therefore a layer of cells is retained against the slide surface when the centrifugation is stopped and the sample suspension fluid drains back into the holding portion away from the slide surface.

The above and other objects of the present invention will become more readily appreciated and understood from a consideration of the following detailed description of preferred and modified forms of the present invention when taken together with the accompanying drawings in which:

BRIEF DESCRIPTION OF THE DRAWINGS

FIG. 1 is an exploded view of a large volume cytological centrifuge chamber assembly in accordance with the invention preliminary to bonding the gasket to the end surface of the chamber;

FIG. 2 is a side view of an upright cytology chamber in accordance with the invention;

FIG. 3 is a face or front view of the flange portion showing the discharge opening of the cytology chamber shown in FIG. 2;

FIG. 4 is a rear view of the chamber shown in FIG. 2 in accordance with the invention.

DETAILED DESCRIPTION OF PREFERRED EMBODIMENT

Figure 5:
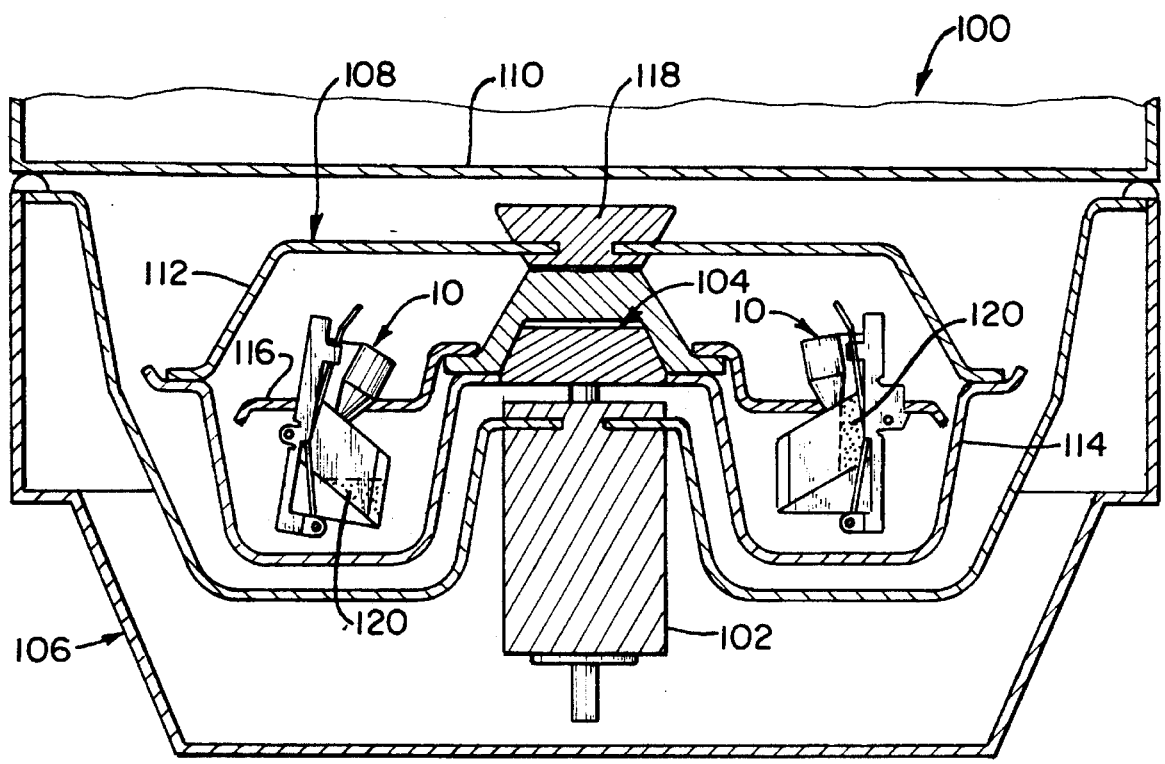
FIG. 5 is a sectional view of a cytocentrifuge which carries a plurality of the cytology chamber assemblies shown in FIG. 1.

Referring in more detail to the drawings, there is shown by way of illustrative example in FIG. 1 a preferred form of chamber assembly 10 in accordance with the invention. The assembly 10 includes a sample chamber 12, a gasket 14 and a microscope slide 16 releasably sandwiched together by a spring clip chamber holder 18. This chamber holder 18 is conventional in design and is merely exemplary of holders in commercial use today.

The chamber assembly 10 is utilized in a cytocentrifuge 100 such as is illustrated in section in FIG. 5. The cytocentrifuge 100 carries a vertically mounted centrifuge motor 102 with a vertically oriented spindle 104 in a lower housing 106. A sealed centrifuge head 108 rides on the end of the motor spindle 104. The head 108 is removable when the centrifuge is at rest. An access cover 110 over the lower housing 106 encloses the rotating parts and protects the operator during centrifuge operation.

The head 108 has a removable top 112 and an annular, bowl shaped bottom 114. The head 108 typically contains an even number of sample chamber assemblies 10 spaced symmetrically about the centrifuge spindle axis in a carrier plate 116. The bowl shaped bottom 114 has a central hub 118 which supports the carrier plate 116 in turn positioning the chamber assemblies 10 symmetrically around the inside of the annular bottom 114. When the top 112 is installed on the bottom 114, all of the sample chamber assemblies 10 are completely sealed inside. The head 108 can then be installed on the spindle 104 in the cytocentrifuge 100 for centrifugal operation in which the entire head 108 is rotated.

The left hand sample chamber assembly 10 shown in FIG. 5 is illustrated in the "at rest" position in which a liquid cytology sample volume 120, typically about 6 milliliters, is only affected by gravity. The right hand sample chamber assembly 10 is illustrated as it would appear during cytocentrifuge operation. In this case the sample volume 120 is primarily affected by centrifugal force and is thus shown against the upright microscope slide surface.

The reader should now refer to FIGS. 2 through 4 wherein various views of the sample chamber 12 in accordance with the preferred embodiment of the invention are shown separate from the assembly 10. The sample chamber 12 is a unitary body for receiving and holding a liquid sample volume 120 of up to about 10 milliliters. It is preferably a molded, one piece body of a plastic which is inert to biological materials such as polyethylene. The chamber 12 has a sample holding portion 20, a liquid suspension-receiving funnel 22 through which the sample volume 120 is guided into the holding portion 20, and a generally flat flange member 24. The flange member 24 is preferably a flat, rigid strip of plastic material having approximately the length and width dimensions of a conventional microscope slide. The flange member 24 supports the holding portion 20 and provides a clamping surface for the holder to clamp the chamber and gasket against the slide 16. In addition, the flange member 24 provides support for the funnel 22 via a vertical gusset 26 extending between the back surface of the flange member 24, the holding portion 20 and the funnel 22. The flange member 24 has a discharge opening 28 therethrough from the holding portion 20.

The holding portion 20 is defined by a pair of spaced vertical sidewalls 30, a bottom wall 32, a back wall 34 spaced from the opening 28, a top wall 36 through which the funnel 22 communicates into the holding portion and the opening 28 in the flange 24. The sidewalls 30, bottom wall 32, and top wall 36 join the flange member 24 and define the opening 28. The bottom wall 32 and the top wall 36 are generally parallel and both extend in cantilevered fashion downward at an acute angle from the flange portion 24. These walls are also preferably tapered toward the back wall 34. The back wall 34 is generally upright and parallel to the flange portion 24.

The holding portion 20 contains a series of three vertically spaced baffle plates 38, 40, and 42 oriented generally parallel to the bottom wall 32. These baffle plates are alternatingly each cantilever supported off of and fully joined to one of the sidewalls 30 along one side of the baffle plate. Thus, as viewed from the flange 24, Figure 3, the lowest baffle plate 38 is joined to the left hand sidewall 30. The second or middle baffle plate 40 is joined to the right hand sidewall 30, and the upper baffle plate 42 is joined to the left hand sidewall 30. All of the plates 38, 40, and 42 have their rear ends joined to the back wall 34 so that liquid passing through the opening 43 from the funnel 22 into the holding portion 20 must flow across first the upper baffle plate 42, across the middle baffle plate 40 and finally across the lowest baffle plate 38 before reaching the bottom wall 32.

The front end 44 of each of the baffle plates 38, 40 and 42 is free and directly faces the discharge opening 28 through the flange member 24. This series of baffle plates creates a tortuous path of surfaces over which the liquid sample 120 must pass. In addition, once the sample has been introduced, and the sample volume 120 covers portions of at least one of the baffle plates, the plates 38, 40 and 42 define a spaced series of inclined ledges upon which sedimented materials will come to rest that are distributed above the bottom of the holding portion 20 of the chamber 12. When the chamber assembly 10 is then centrifuged, the sedimented materials will simply migrate outwardly toward the opening 28 along the upper surfaces of the baffle plates 38, 40 and 42. This material then travels directly to the portion of the microscope slide opposite the free end 44 of the baffle plate over which it passed. Thus any sedimented material will be distributed to different positions on the microscope slide depending upon which baffle plate the material may have come to rest.

Cellular material that remains in suspension is not adversely affected by the baffle plates 38, 40 and 42 since, during centrifugation, most of the plates are not in the sample volume and the plates are inclined at a very steep angle with respect to the direction of centrifugal force.

The funnel 22 is an elongated open tube which has an open mouth 46 for receiving the tip of a pipette. The tube preferably converges to a smaller circular opening 43 through the top wall 36 into the holding portion 20. The axis of the tubular funnel 22 is preferably normal to the top wall and the baffle plates and is positioned so that, if extended downward, it would pass through the free end of the upper baffle plate 42.

In another aspect of the invention, referring back to FIG. 1, the chamber 12 is sealed to a microscope slide 16 by means of a gasket 14. The gasket 14 preferably is rectangular in shape and is sized to cover the surface 48 of the flange member 24. The gasket 14 has a rectangular opening 50 therethrough matching in size and positioned to register with the discharge opening 28. The gasket 14 is preferably bonded or otherwise permanently adhered in advance to the facing surface 48 of the flange member 24, since it is undesirable to use a chamber more than once because of contamination considerations. The gasket 14, which is preferably a closed cell foam plastic sheet material, may be ultrasonically or adhesively bonded with a double faced adhesive to the flange member 24.

The holder 18 is of conventional design, and typically is a channel-shaped sheet metal body which has a pair of side rails 52 spaced to receive the slide 16, the gasket 14, and the flange member 24 therein. A wire spring clip 54 is pivotally attached to the side rails 52 at one end. When the slide 16, gasket 14 and flange portion 24 of the chamber 12 are stacked together and sandwiched between the side rails 52, the clip wire 54 can be rotated, passing over the holding portion 20 and the funnel 22 to a latched position engaging tabs (not shown) on the side rails 52 of the channel shaped holder 18 to releasably clamp the flange member 24 to the slide 16. The holder 18 also includes a cross bar 56 supported by the side rails 52. This bar 56 fits into the carrier 116 shown in FIG. 5 to permit the partial rotation of the assembly 10 as shown during centrifugation.

Various changes and modifications to the assembly 10 of the invention may be made without departing from the scope of the present invention. For example, a different number of baffle plates may be distributed in the holding portion 20 of the chamber 12. The baffle means alternatively may be constructed of a single, folded sheet of material placed in the holding portion 20. The baffle may also be created by having the sidewalls themselves undulate back and forth under the funnel opening 43. The gasket 14 need not be rectangular in shape as is shown in FIG. 1 but may be any shape so long as it surrounds the opening 28 and provides a seal when the slide 16 and flange portion 24 are pressed together in the holder 18. The gasket 14 may also be made of any material which provides a seal and is generally inert to biological material. Following centrifugation, the operator either may discard the liquid from the chamber or decant into a beaker and use the supernatant for other tests, such as, bronchial washing or bacteriological studies.

It is therefore to be understood that the above and other modifications and changes may be made in the unitary chamber assembly and method in accordance with the invention without departing from the spirit and broad scope of the invention as defined by the appended claims. All patents and other printed publications referred to herein are hereby incorporated by reference in their entirety.

I claim:

1. A unitary disposable cytological sample chamber for receiving a sample of biological material in a liquid suspension and distributing said biological material onto a microscope slide during centrifugation of said suspension in said chamber in a centrifuge, said chamber comprising a sample holding portion, a liquid suspension-receiving funnel through which said sample is directed into said holding portion of said chamber, a generally flat, solid flange member defining a support surface and having a discharge opening in said flange member in communication with said holding portion, said holding portion having a pair of spaced sidewalls, a bottom wall, a back wall spaced from said opening and staggered baffle means for directing said sample along a tortuous path upon which said biological material may settle until said chamber is centrifuged. Whereby said biological material is centrifugally transported through said discharge opening and distributed onto said microscope slide.

2. The chamber according to claim 1, wherein said baffle means comprises a plurality of vertically spaced baffle plate members generally parallel to said bottom wall, each of said baffle plate members being supported from said back wall and alternatingly one or the other of said sidewalls, whereby as said liquid suspension sample is introduced into said chamber said sample flows from said funnel sequentially across each of said spaced baffles to reach said bottom wall.

3. The chamber according to claim 2, wherein said baffle plate members are flat plates.

4. The chamber according to claim 3, wherein a gasket on said flange member has an aperture therethrough in registry with said opening, said gasket forming a seal against said microscope slide around said opening when said flange member is pressed against said microscope slide, and securing means for fixing said gasket to said flange whereby said gasket is integrally united with said support surface.

5. The chamber according to claim 4, wherein said gasket is a closed cell foam material.

6. The chamber according to claim 5, wherein said gasket is permanently bonded to said support surface.

7. A unitary disposable cytological sample chamber for receiving a sample of biological material in a liquid suspension and distributing said biological material onto a microscope slide during centrifugation of said suspension in said chamber in a centrifuge, said chamber comprising a sample holding portion, a liquid suspension-receiving funnel through which said sample is directed into said holding portion of said chamber, a generally flat, solid flange member defining a support surface and having a discharge opening in said flange member in communication with said holding portion, said holding portion having a pair of spaced vertical sidewalls, a bottom wall, a back wall spaced from said opening and a plurality of vertically spaced baffle plate members generally parallel to said bottom wall, each of said baffle plate members being supported from said back wall and alternatingly one or the other of said sidewalls, whereby as said liquid suspension sample is introduced into said chamber said sample flows from said funnel sequentially across each of said spaced baffles to reach said bottom wall permitting some of said biological material to be deposited on said baffles and, when said chamber is centrifuged, said deposited material is centrifugally transported through said discharge opening and distributed onto said microscope slide from said baffles.

8. The chamber according to claim 7, further wherein a gasket on said flange member has an aperture therethrough in registry with said opening, said gasket forming a seal around said opening when said flange member is pressed against said microscope slide and securing means for fixing said gasket to said flange whereby said gasket is permanently affixed to said support surface.

9. The chamber according to claim 8, wherein said bottom wall of said holding portion is cantilever supported from said flange at an acute angle to said flange.

10. The chamber according to claim 9, wherein said baffle plate members are flat.

11. In a centrifuge including a plurality of sample holders mounted on a rotating carrier, each said sample holder having clamping means releasably receiving a cytology chamber containing a liquid suspension of biological material therein and a microscope slide against said chamber, the improvement comprising:

said cytology chamber having a liquid sample-receiving funnel leading to a sample holding portion and a generally flat flange having a discharge opening therethrough from said holding portion for mating with one surface of a microscope slide wherein said holding portion includes baffle means for directing said sample along a tortuous path of surfaces in said holding portion upon which said biological material may settle until said chamber is centrifuged, whereby said biological material is centrifugally transported through said discharge opening and distributed onto said microscope slide.

12. The improvement according to claim 11, wherein said baffle mean comprises a plurality of vertically spaced baffle plate members, each of said baffle plate members being supported from said back wall and alternatingly one or the other of said sidewalls, whereby as said liquid suspension sample is introduced into said chamber through said funnel said sample flows sequentially across each of said spaced baffle plate members to reach said bottom wall.

13. The improvement according to claim 12, wherein said baffle plate members are flat plates.

14. The improvement according to claim 13, further comprising a gasket on said flange member having an aperture therethrough in registry with said opening, said gasket forming a seal around said opening when said flange member is pressed against said microscope slide and securing means for fixing said gasket to said flange whereby said gasket is integrally united with said support surface.

15. The improvement according to claim 14, wherein said gasket is a closed cell foam material.

16. The improvement according to claim 14, wherein said gasket is permanently bonded to said support surface.

* * * * *